United States Patent [19]

Pedersen

[11] Patent Number: 4,836,907
[45] Date of Patent: Jun. 6, 1989

[54] ELECTROCHEMICAL MEASURING ELECTRODE DEVICE FOR SIMULTANEOUSLY MEASURING THE PARTIAL PRESSURES OF TWO GASSES

[75] Inventor: Knud G. Pedersen, Lyngby, Denmark

[73] Assignee: Radiometer A/S, Copenhagen, Denmark

[21] Appl. No.: 129,428

[22] Filed: Nov. 25, 1987

Related U.S. Application Data

[63] Continuation of Ser. No. 891,774, Jul. 30, 1986, abandoned, which is a continuation of Ser. No. 720,044, Apr. 4, 1985, abandoned, which is a continuation of Ser. No. 511,678, Jul. 7, 1983, abandoned.

[30] Foreign Application Priority Data

Jul. 14, 1982 [DK] Denmark .............................. 3170/82

[51] Int. Cl.[4] .......................... G01N 27/52; A61B 5/04
[52] U.S. Cl. ..................................... 204/412; 204/403; 204/415; 128/635
[58] Field of Search ............... 204/403, 412, 415, 416, 204/417, 418, 419, 420; 128/635

[56] References Cited

U.S. PATENT DOCUMENTS

| | | | |
|---|---|---|---|
| 4,197,853 | 4/1980 | Parker | 204/412 X |
| 4,274,418 | 6/1981 | Vesterager et al. | 204/415 X |
| 4,280,505 | 7/1981 | Dali et al. | 128/635 |
| 4,333,473 | 6/1982 | Eberhard et al. | 204/412 X |

FOREIGN PATENT DOCUMENTS

| | | | |
|---|---|---|---|
| WO81/02831 | 10/1981 | PCT Int'l Appl. | 204/403 |
| 0039136 | 11/1981 | PCT Int'l Appl. | 204/403 |
| 2005418A | 7/1977 | United Kingdom | 204/412 |
| 2021784A | 5/1978 | United Kingdom | 204/403 |

OTHER PUBLICATIONS

Beran et al, "Investigation . . . Newborns"; Birth Defects, Original Article Series, vol. XV, No. 4, p. 421-430.
Parker et al., "Single . . . $PCO_2$", Birth Defects, Orginal Series, vol. XV, No. 4, pp. 109-116.

*Primary Examiner*—Nam X. Nguyen
*Attorney, Agent, or Firm*—Bryan, Cave, McPheeters & McRoberts

[57] ABSTRACT

An electrochemical electrode device for simultaneously measuring the partial pressures of two gasses in a medium of limited gas availability one of which is measured potentiometrically and another one of which is measured polarographically comprises an electrode body (18) constituting a reference electrode relative to a pH-electrode (19) of a potentiometric electrode system, and a anode relative to a cathode (20) of a polarographic electrode system. Furthermore, the electrode device comprises an electrolyte solution (28) enclosed between the electrode body and a membrane (30). The membrane comprises a basic membrane layer (31), preferably of polytetrafluoroethylene (PTFE) or fluoroethylenepropylene (FEP) of a thickness of about 12 μm, and a covering (32), preferably a polypropylene layer of a thickness of about 15 μm, which covers part of the basic membrane layer so that an uncovered area (34) is constituted in front of the pH-electrode. The uncovered area constitutes a first membrane part showing high permeability to the first gas and constitutes together with the potentiometric electrode system and the electrolyte solution a first measuring system for measuring the partial pressure of the first gas. A covered area of the basic membrane layer constitutes together with its covering a second membrane part showing low permeability to the second gas and is arranged in front of the exposed measuring surface of the cathode so as to restrict the diffusion of the second gas to the cathode and together with the polarographic electrode system and the electrolyte solution to constitute a second measuring system for measuring the partial pressure of the second gas.

23 Claims, 2 Drawing Sheets

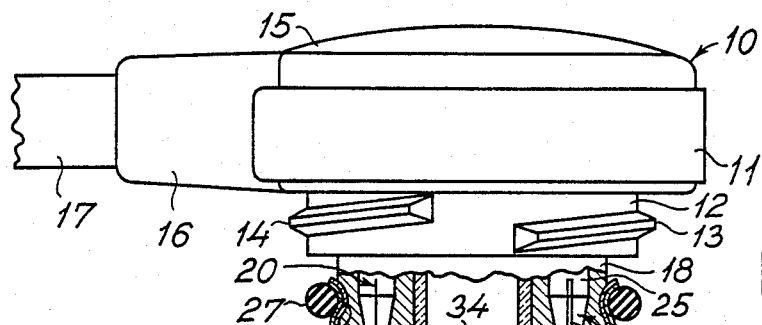
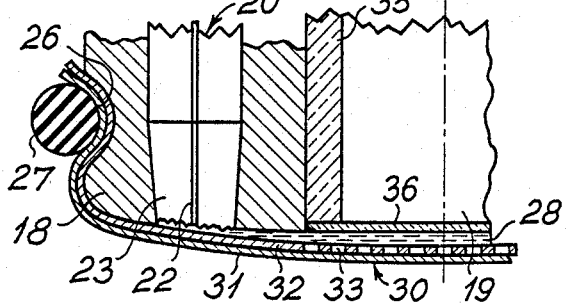
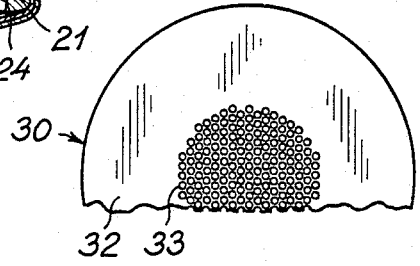
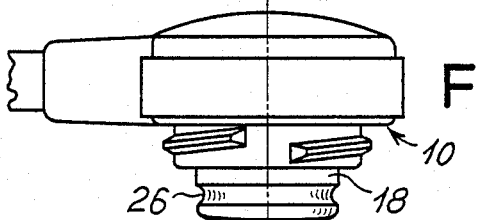
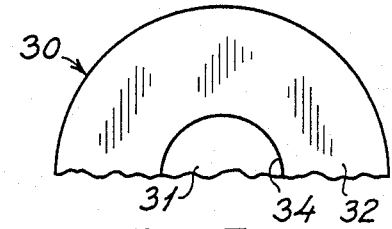
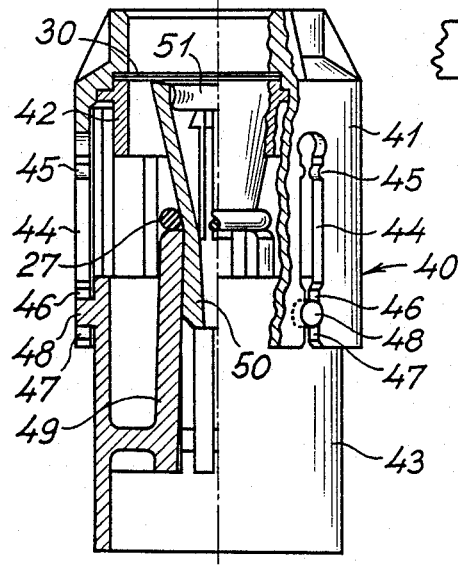
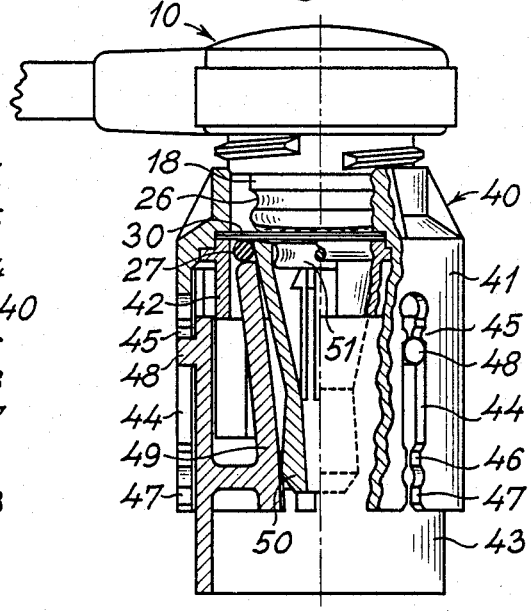

ELECTROCHEMICAL MEASURING ELECTRODE DEVICE FOR SIMULTANEOUSLY MEASURING THE PARTIAL PRESSURES OF TWO GASSES

This is a continuation, of U.S. application Ser. No. 891,774, filed 07/30/86, abandoned which is a continuation of U.S. application Ser. No. 720,044, filed Apr. 4, 1985, now abandoned, which is a continuation of U.S. application Ser. No. 511,678, filed July 7, 1983, now abandoned.

The present invention relates to an electrochemical measuring electrode device for simultaneously measuring the partial pressures of two gasses in a medium of limited gas availability one of which is measured potentiometrically and another one of which is measured polarographically.

BACKGROUND OF THE INVENTION

In the potentiometric measurement of the partial pressure of a gas which in an aqueous solution generates an acid or a base, an electrochemical measuring electrode device is employed which, in accordance with the Stow-Severinghaus principle, comprises a potentiometric electrode system including a pH-electrode and a reference electrode, an electrolyte solution which communicates with the electrode system, and a membrane which is adapted to enclose the electrolyte solution in contact with the electrode system and which is permeable to the gas to be measured.

Correspondingly, in the polarographic measurement of the partial pressure of a gas, an electrochemical measuring electrode device is employed which, in accordance with the Clark-measuring principle, comprises a polarographic electrode system including a cathode and an anode, an electrolyte solution which communicates with the electrode system, and a membrane which is adapted to enclose the electrolyte solution in contact with the electrode system and which is permeable to the gas to be measured.

In operation of a Stow-Severinghaus electrode device for potentiometrically measuring the partial pressure of gas which in an aqueous solution generates an acid or a base, especially carbon dioxide, the gas in question permeates the membrane and is dissolved in the electrolyte solution, thereby causing a shift of pH, e.g.:

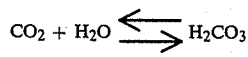

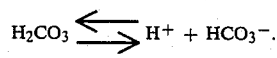

Correspondingly, in operation of a Clark-electrode device, e.g. when measuring the partial of $O_2$, the gas to be measured permeates the membrane and is reduced at the cathode, i.e. the gas in question is consumed by the polarographic electrode system, e.g.:

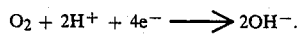

Recent developments in electrochemical measuring electrode devices, especially for clinical measurement of gas partial pressures in blood, have provided devices for simultaneously measuring the partial pressures of two gasses, normally $O_2$ and $CO_2$, one of which is measured potentiometrically and another one of which is measured polarographically.

Thus, e.g. UK patent application No. 2.005.418 A discloses an electrode device for simultaneous measurement of $pCO_2$ and $pO_2$, in particular transcutaneously, and having a first electrode which is a pH-responsive electrode, a second electrode capable of electrochemically reducing oxygen, a reference electrode for each of, or common to, the pH-responsive electrode and the oxygen reducing electrode, an electrolyte in contact with the electrodes, and a membrane permeable to oxygen and carbon dioxide.

International Patent Application No. PCT/DK/81/00035 discloses an electrode device for measuring the partial pressure of oxygen and of a gas which in an aqueous solution generates an acid or a base, such as carbon dioxide, in particular transcutaneously, the device comprising potentiometric and polarographic measuring electrode systems of the above types and further comprising a compensation electrode adapted to electrochemically consume hydroxyl ions in an amount stoichiometrically equal to the amount of hydroxyl ions generated at the oxygen reducing electrode, i.e. the cathode in order to eliminate the influence of the hydroxyl ions generated at the oxygen reducing electrode on the pH of the electrolyte solution and, thus, on the measurement of the partial pressure of said gas which in an aqueous solution generates an acid or a base. In an article: "A Combined Transcutaneous $pO_2$-$pCO_2$ Electrode with Electrochemical $HCO_3^-$ Stabilisation", by John W. Severinghaus, published in Journal of Applied Physiology, vol 51, No. 4, pp 1027–1032, March 1981, a similar combined electrochemical measuring electrode device comprising a compensation electrode is disclosed.

The potentiometric measuring principle and the polarographic measuring principle are inherently different from each other. According to the potentiometric pH measuring principle, an equilibrium change caused by a change of the partial pressure of the gas in question is detected by measuring the change of pH in the electrolyte solution. Contrary to this, the polarographic measuring principle involves continuous consumption of the gas the partial pressure of which is to be measured; consequently, when measuring the partial pressure of a gas in a medium of limited gas availability, such as transcutaneous measurements, or measurements on small blood samples, problems may arise in correlating the current generated by reduction of the gas in question at the cathode of the polarographic electrode system and the steady state gas partial pressure outside the membrane since a large consumption of gas, which corresponds to a large current, influences the steady state outside the membrane and, thus, causes a decrease of the gas partial pressure outside the membrane, thereby incurring erroneous measuring results. For this reason, the membrane of polarographic electrode devices is normally constructed of a material showing relatively low permeability to the gas to be measured in order to reduce the consumption of the gas in question.

The present invention provides an electrochemical measuring electrode device which permits highly accurate and highly responsive measurements of the partial pressures of two gasses in a medium of limited gas availability one of which is measured potentiometrically and another one of which is measured polarographically.

SUMMARY OF THE INVENTION

There is provided an electrochemical measuring electrode device for simultaneously measuring the partial pressures of two gases in a medium of limited gas availability one of which is measured potentiometrically and another one of which is measured polarographically, comprising:

an electrode body, a potentiometric electrode system arranged in said body and comprising a reference electrode and a pH-electrode, a polarographic electrode system arranged in said body and comprising a cathode and an anode, an electrolyte solution communicating with said two electrode systems and enclosed substantially between said body and a membrane, said membrane comprising a first part showing high permeability to said first gas, arranged in front of the exposed measuring surface of the pH-electrode of said first electrode system and together with said first electrode system and said electrolyte solution constituting a first measuring system for measuring the partial pressure of said first gas, and a second part showing low permeability to said second gas, arranged in front of the exposed measuring surface of the cathode of said second electrode system so as to restrict the diffusion of said second gas to the cathode and together with said second electrode system and said electrolyte solution constituting a second measuring system for measuring the partial pressure of said second gas, the dimensions of the exposed measuring surface of the cathode and the permeability of said second membrane part being so adapted to one another that the response of said second measuring system when measuring in a medium of limited gas availability is substantially identical to the response of said second measuring system when measuring in a medium of unlimited gas availability, and said first and said second measuring systems having response time characteristics of the same order of magnitude.

The gas, the partial pressure of which is measured polarographically, is normally oxygen, and the gas, the partial pressure of which is measured potentiometrically, is normally carbon dioxide. In the following description, reference will, therefore, be made to these two gases.

In the present context, the term "substantially identical", as used in relation to the response of the polarographic measuring system in a medium of limited gas availability in relation to a medium of unlimited gas availability indicates responses which are the same within practically acceptable limits for the type of measurement in question. Thus, e.g., when transcutaneously measuring the partial pressure of oxygen, a linear relation between oxygen partial pressure measured at skin surface and oxygen partial pressure measured arterially with a coefficient of proportionality of 0.85 constitutes a high degree of fulfilment of the claim to "substantial identity".

In the present context, the term "of the same order of magnitude" is used about quantities which differ from each other at the most by a factor 10, and correspondingly, the term "having response time characteristics of the same order of magnitude" indicates response time constants differing from each other at the most by a factor 10.

In a preferred embodiment of the invention, the cathode is a microcathode. The term "micro-cathode" indicates a cathode of which at least one dimension of its exposed measuring surface is so small that the gas consumption at the cathode does not cause any substantial depletion of the gas to be measured polarographically. This dimension may typically be less than e.g. 75 $\mu m$.

The exposed measuring surface of the cathode may have any appropriate shape, e.g. be quadrangular, triangular, elongated, ring-shaped or helical. However, it is preferred that the exposed measuring surface of the cathode is substantially circular, preferably a microcathode surface of a diameter of less than 75 $\mu m$, more preferably of a diameter of about 25 $\mu m$, thus constituting an exposed measuring area of less than $4 \times 10^{-3}$ mm$^2$, more preferably about $0.5 \times 10^{-3}$ mm$^2$. By employing a micro-cathode, the sensitivity of the polarographical measuring system may be reduced to 5 pA/mm Hg or less. In combination with suitable selection of the second membrane part with respect to it permeability such as discussed below, such small sensitivity and the corresponding small $O_2$ consumption result in highly linear measurements of the partial pressure of oxygen and thus in a high degree of identity between a measurement in a medium of limited oxygen availability and a measurement in a medium of unlimited oxygen availability.

In practice, the fulfilment of the above-mentioned requirement that the response time characteristics of the two measuring electrode systems be within the same order of magnitude will normally be based on a potentiometric measuring system which is highly responsive and a corresponding adaption of the polarographic measuring system to high responsiveness, but with due consideration of the necessity of a sufficiently low oxygen permeability of the second membrane part in relation to the oxygen consumption of the cathode to retain the substantial identity between a measurement in a medium of limited oxygen availability and a measurement in a medium of unlimited oxygen availability. As will be evident from the detailed description which follows, the present invention has provided electrode devices for transcutaneous simultaneous measurement of the partial pressures of $O_2$ and $CO_2$, which have the same response time constants of the potentiometric and polarographic measuring systems of the order of 0.5 min.

For most clinical purposes, the requirement of high responsiveness is mandatory, and it is also important that the response time characteristics of the potentiometric and polarographic measuring systems are of the same order of magnitude. This applies both to transcutaneous measurements and to measurements on small blood samples, i.e. blood samples of less than 100 $\mu l$, e.g. 50 $\mu l$, where the present invention provides highly linear and highly responsive measurements of the partial pressures of $O_2$ and $CO_2$.

One of the main features of the present invention is the selection of individual membrane parts for the polarographic and the potentiometric measuring systems to obtain a relatively low and a relatively high permeability, respectively, to the respective gases in question.

Since most materials showing high permability to the gas to be measured potentiometrically, e.g. $CO_2$, also show high permeability to the gas to be measured polarographically, e.g. $O_2$, and vice versa, the membrane may consist of a basic membrane layer and a covering which covers part of the basic membrane layer, an uncovered area of the basic membrane layer constituting the said first membrane part, and a covered area of the basic membrane layer together with its covering constituting the said second membrane part.

The first membrane part may be made of any material showing high permeability to the gas to be measured potentiometrically, such as silicon rubber or low density polyethylene. However, the first membrane part is preferably made of polytetrafluoroethylene (PTFE) or fluoroethylenepropylene (FEP) of a thickness of less than 50 $\mu$m, such as 8–50 $\mu$m, preferably 8–25 $\mu$m, most preferably about 12 $\mu$m, or similar materials showing equivalent permeability characteristics. By this, a permeability relative to $O_2$ diffusion and $CO_2$ diffusion of at least $80 \times 10^{-9}$ cm$^3$/cm$^2 \times$ s $\times$ cm Hg and at least $200 \times 10^{-9}$ cm$^3$/cm$^2 \times$ s $\times$ cm Hg, respectively thickness less than 50 $\mu$m), such as $80 \times 10^{-9} - 500 \times 10^{-9}$ cm$^3$/cm$^2 \times$ s $\times$ cm Hg and $200 \times 10^{-9} - 1250 \times 10^{-9}$ cm$^3$/cm$^2 \times$ s $\times$ cm Hg, respectively (thickness 8–50 $\mu$m), preferably a permeability of $160 \times 10^{-9} - 500 \times 10^{-9}$ cm$^3$/cm$^2 \times$ s $\times$ cm Hg and $400 \times 10^{-9} - 1250 \times 10^{-9}$ cm$^3$/cm$^2 \times$ s $\times$ cm Hg, respectively (thickness 8–25 $\mu$m), most preferably a permeability of $330 \times 10^{-9}$ cm$^3$/cm$^2 \times$ s $\times$ cm Hg and $830 \times 10^{-9}$ cm$^3$/cm$^2 \times$ s $\times$ cm Hg, respectively (thickness about 12 $\mu$m), is obtained.

The second membrane part may comprise any material showing low permeability to the gas to be measured polarographically, in particular oxygen, such as low density polyethylene, fluoroethylenepropylene (FEP) or polytetrafluoroethylene (PTFE) of an appropriate thickness. However, the second membrane part preferably comprises a polypropylene layer of a thickness of 5–30 $\mu$m, preferably 5–20 $\mu$m, most preferably about 15 $\mu$m, or similar materials showing equivalent permeability characteristics. By this, a permeability relative to $O_2$ diffusion and $CO_2$ diffusion of $33 \times 10^{-9} - 200 \times 10^{-9}$ cm$^3$/cm$^2 \times$ s $\times$ cm Hg and $160 \times 10^{-9} - 1000 \times 10^{-9}$ cm$^3$/cm$^2 \times$ s $\times$ cm Hg, respectively (thickness 5–30 $\mu$m), preferably $50 \times 10^{-9} - 200 \times 10^{-9}$ cm$^3$/cm$^2 \times$ s $\times$ cm Hg and $250 \times 10^{-9} - 1000 \times 10^{-9}$ cm$^3$/cm$^2 \times$ s $\times$ cm Hg, respectively (thickness 5–20 $\mu$m), most preferably $66 \times 10^{-9}$ cm$^3$/cm$^2 \times$ s $\times$ cm Hg and $330 \times 10^{-9}$ cm$^3$/cm$^2 \times$ s $\times$ cm Hg, respectively (thickness about 15 $\mu$m), is obtained.

From the above is seen that a polytetrafluoroethylene (PTFE) or fluoroethylenepropylene (FEP) layer of a thickness of 8–50 $\mu$m provides a permeability relative to $CO_2$ diffusion of $200 \times 10^{-9} - 1250 \times 10^{-9}$ cm$^3$/cm$^2 \times$ s $\times$ cm Hg and that a polypropylene layer of a thickness of 5–30 $\mu$m provides a permeability relative to $O_2$ diffusion of $33 \times 10^{-9} - 200 \times 10^{-9}$ cm$^3$/cm$^2 \times$ s $\times$ cmm Hg.

A particularly simple and elegant embodiment of the electrode device according to the invention is obtained when the covering of the basic membrane laye is an annular covering.

Although either side of the membrane assembly may be arranged facing the electrolyte solution, it is preferred that the covering of the basic membrane layer is arranged between the basic membrane layer and the electrode body so that an electrolyte reservoir is obtained in front of the pH-electrode.

In order to keep the membrane and the pH-electrode spaced apart, the uncovered body by means of a spacer.

In a practical and preferred embodiment the spacer may be constituted by a perforated part of the covering.

In order to guarantee an adequate permeation of the gas to be measured potentiometrically, the perforation area of the spacer preferably constitutes at least 50%, preferably 50–70% of said uncovered area in front of the pH-electrode.

In order to reduce the overall dimensions of the electrode device according to the invention and reduce the number of components, thereby reducing the complexity of the measuring electrode device, the reference electrode of the potentiometric electrode system and the anode of the polarographic electrode system may be constituted by the electrode body. In this embodiment having a combined reference electrode and anode, the electrode body is preferably a silver body having a chlorinated surface facing the electrolyte solution and the cathode is preferably a platinum cathode of a diameter of less than 75 $\mu$m, preferably a diameter of about 25 $\mu$m.

For clinical purposes, i.e. when measuring the blood gas partial pressures of $CO_2$ and $O_2$ in accordance with the transutaneous measuring principle, the electrode device according to the invention may be provided with thermostating means for thermostatically controlled heating of the device to an elevated temperature such as a temperature slightly above skin temperature. The thermosetting means may comprise any conventional temperature heating and temperature controlling means, such as a Zener diode or a heating resistor and a thermistor or an NTC resistor, respectively.

In an article: "Investigation of Transcutaneous $O_2$—$CO_2$ Sensors and Their Application on Human Adult and Newborns", by Anthony V. Beran et al., published in: "Birth defects: Original Article Series" Volume XV, No. 4, pages 421–430, copyright 1979 The National Foundation, an electrode device for transcutaneously measuring the partial pressures of $O_2$ and $CO_2$ is disclosed. The electrode device comprises a potentiometric electrode system comprising a pH-glass electrode arranged centrally within a silver body which constitutes a reference electrode, and a polarographic electrode system comprising an anode constituted by said silver electrode body and a cathode constituted by a gold wire of an outer diametre of 0.1 cm. The membrane is composed of a 75 $\mu$m polyvinylchloride (PVC) sheet onto which a circular 12.5 $\mu$m silicone rubber membrane is attached by means of a ring of Scotch adhesive transfer tape. In the centre of the adhesive ring, the PVC sheet is perforated with approximately 20 holes with diameters of 0.2 mm.

However, this known $O_2$—$CO_2$ measuring electrode device does not offer the advantages which are characteristic to the devices according to the present invention. Thus, when measuring, the pO$_2$ measuring system of the electrode device generates a large current caused by its large cathode (the electrode device has a sensitivity of 120 pA/mm Hg in the range of 0–150 mm Hg) and, thus, a considerable amount of $O_2$ is consumed, which, as explained above, tends to cause erroneous measurements. The article does not indicate anything about this problem relating to the polarographic measuring system, much less suggest any solution of the problem. The membrane materials disclosed in the article are not of a kind which would permit the obtainment of highly responsive polarographic and potentiometric measurements, such as will be evident from measuring results described in greater detail below.

The present invention also relates to a membrane for an electrochemical measuring electrode device for simultaneously measuring the partial pressures of two gases in a medium of limited gas availability one of which is measured potentiometrically and another one of which is measured polarographically, comprising:
  a first part showing high permeability to said first gas and adapted to be arranged in front of an exposed measuring surface of a pH-electrode of a potentiometric pH-measuring electrode system and, together with said potentiometric pH-measuring electrode system and an electrolyte solution, to constitute a potentiometric measuring system for measuring the partial pressure of said first gas, and a second part showing low permeability to said second gas and adapted to be arranged in front of an exposed measuring surface of a cathode of a polarographic electrode system and, together with said polarographic electrode system and said electrolyte solution, to constitute a polarographic measuring system for measuring the partial pressure of said second gas,
  the permeability of said second membrane part being so adapted relative to the dimensions of the exposed measuring surface of the cathode that the response of said second measuring system when measuring in a medium of limited gas availability is substantially identical to the response of said second measuring system when measuring in a medium of unlimited gas availability, and
  said first and said second parts of the membrane being adapted to provide response time characteristics of said potentiometric measuring system and said polarographic measuring system of the same order of magnitude.

The characteristics of the membrane, as well as the preferred embodiments thereof, are explained in detail above.

Furthermore, the present invention relates to a membrane mounting kit for mounting a membrane on an electrochemical measuring electrode device for simultaneously measuring the partial pressures of two gasses in a medium of limited gas availability one of which is measured potentiometrically and another one of which is measured polarographically, comprising a membrane supporting structure adapted to cooperate with a membrane mounting tool when mounting said membrane on the electrode device, and a membrane having any of the above described characteristics.

Although the membrane supporting structure together with the membrane according to the invention may constitute a single component adapted to be introduced in a membrane mounting tool when mounting the membrane on an electrode device, it is preferred that the membrane supporting structure together with the membrane constitutes a component of a disposable membrane mounting tool.

In a further aspect of the present invention there is provided a method for producing a membrane for an electrochemical measuring electrode device for simultaneously measuring the partial pressures of two gasses one of which is measured potentiometrically and another one of which is measured polarographically comprising: arranging a first and a second membrane layer on top of one another, said first layer showing high permeability to said first gas and said second layer showing low permeability to said second gas, one or more apertures of said second layer leaving an area of said first layer uncovered, and said layers together constituting a membrane having any of the above described characteristics of the membrane according to the invention.

When producing the membrane, a particularly rigid membrane construction is obtained when the two layers are laminated together.

The above-mentioned apertures of the second layer may be provided in the second layer prior to arranging or laminating the two layers together e.g. by Laser shooting. Alternatively, the two layers are arranged or laminated together, one or more holes may be provided in the second layer by Laser shooting.

BRIEF DESCRIPTION OF THE DRAWINGS

The invention will now be further described with reference to the drawings, wherein FIG. 1 is a partly sectional view of a preferred embodiment of an electrochemical measuring electrode device according to the invention, FIG. 2 an enlarged detail of the embodiment shown in FIG. 1, FIG. 3a a plane view of a first embodiment of a membrane according to the invention, FIG. 3b a plane view of an alternative, preferred embodiment of a membrane according to the invention, FIG. 4 the embodiment of the electrochemical measuring electrode device shown to FIG. 1 prior to mounting the membrane thereon by means of a mounting tool, FIG. 5 corresponding to FIG. 4 the electrochemical measuring electrode device and the mounting tool during mounting the membrane, FIG. 6 a diagram showing $CO_2$- and $O_2$-responses of a conventional electrochemical measuring electrode device and of a preferred embodiment of the electrochemical measuring electrode device according to the invention, respectively, when measuring in vitro, and FIG. 7 a diagram showing measurements obtained by means of the electrochemical measuring electrode device according to the invention, when measuring in vivo.

DETAILED DESCRIPTION OF THE DRAWINGS

Figure 6:
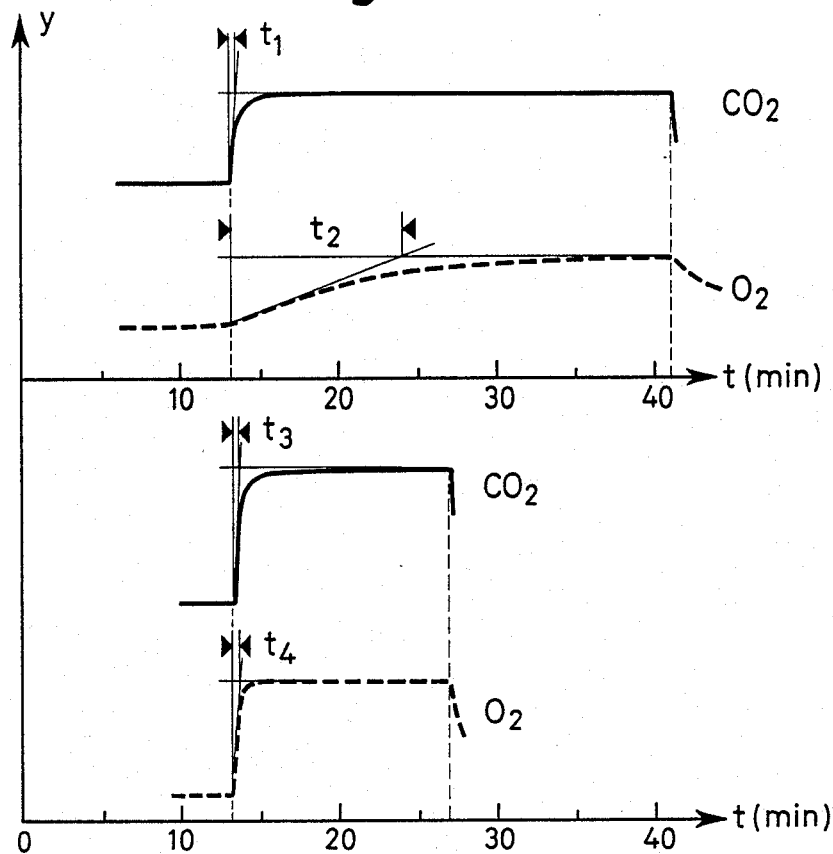

In FIG. 1 a preferred embodiment of an electrochemical measuring electrode device according to the invention is shown designated 10 in its entirety. The electrode device 10 comprises an electrode housing 11 made of plastics, e.g. acrylonitril-butadiene-styrene plastics (ABS plastics) and at its lower end, the housing 11 has a reduced diameter part 12 which is provided with external threads 13 and 14 adapted to cooperate with corresponding internal threads of a fixing ring (not shown in the drawing). The upper part of the housing 11 is provided with a lid 15 cast or welded to the electrode housing 11. Furthermore, the housing 11 is provided with an externally protruding stub 16 which is adapted to cooperate with a multicore cable 17 for electrical connection to external equipment.

Within the electrode housing 11, an electrode body 18 is arranged protruding from the lower end of the reduced diameter part 12 of the electrode housing 11. The electrode body 18 is a silver body having a chlorinated lower surface. Within the electrode housing 11, an interior space defined between the upper surface of the electrode body 18 and the lower side of the lid 15 is filled up with a casting of e.g. epoxy (not shown in the drawing). Furthermore, the electrode body 18 is provided with thermostating means, i.e. a heating means and a temperature controlling means, such as a heating resistor or a Zener diode and a NTC resistor, respectively (not shown in the drawing). Such thermostating means are described in U.S. Pat. No. 4.324.256.

In a central hole of the electrode body 18, a pH-glass electrode 19 is arranged. The electrode body 18 and the pH-glass electrode 19 together constitute an electrode system for potentiometrically measuring the partial pressure of a gas which in an aqueous solution generates an acid or a base, such as $CO_2$. The pH-glass electrode 19 may be of the kind described in applicant's copending PCT application PCT/DK82/00024 also described in example 1 below and comprises a main tube 35 and a glass-membrane 36 attached thereto.

Furthermore, the electrode device comprises a polarographic measuring electrode system constituted by a cathode assembly 20 and the above described electrode body 18. The cathode assembly 20, which is shown in greater detail in FIG. 2, includes a metallic wire 22, e.g. a platinum wire, arranged within a tubular body 23. The cathode assembly 20 is preferably produced by arranging the metallic wire 22 in the tubular body 23 and thereupon heating the assembly to such a temperature that the tubular body 23 melts into intimate contact with the metallic wire 22. The tubular body 23 is secured within a throughgoing bore of the electrode body 18, e.g. by gluing or casting, preferably while maintaining a good thermal conductivity, e.g. by means of a heat conductive epoxy resin, and is made of an insulating material, such as glass.

In the embodiment of the invention shown in FIG. 1, an compensation electrode assembly designated 21 of the kind described in applicant's above mentioned copending PCT application PCT/DK81/00035 is also included. However, it should be emphasized that the compensation electrode assembly is not mandatory to the present invention and may be omitted. The compensation electrode assembly 21 includes a metallic wire 24, preferably a platinum wire embedded within a tubular body 25 which also serves securing and insulating purposes and is preferably produced in the above described manner. As is evident from FIG. 1, the diameter of the metallic wire 24 of the compensation electrode assembly 21 is significantly larger than the diameter of the metallic wire 22 of the cathode assembly 20. Thus, the exposed lower surface of the metallic wire 22 constitutes a socalled micro-cathode, e.g. a cathode having an exposed circular measuring area of a diametre of less than 75 $\mu$m and, thus, an area of less than $4\times10^{-3}$ mm.

At its outer circumferential surface, the electrode body 18 is provided with an annular recess 26 which is adapted to cooperate with an O-ring 27 for fastening a membrane which is designated 30 relative to the electrode body 18. The O-ring 27 also serves to seal a space defined between the membrane 30 and the lower surface of the electrode body 18 in which an electrolyte solution 28 is confined. As is evident from FIG. 2, the membrane 30 is composed of two layers designated 31 and 32 and constituting an outer layer and an inner layer, respectively. The outer layer 31 constitutes a basic component of the membrane and is made of a material showing high permeability to the gas which is to be measured by means of the potentiometric electrode system, i.e. showing high permeability to $CO_2$. As indicated above, most materials showing high permeability to $CO_2$ also show high permeability to $O_2$ and vice versa. Therefore, the inner layer 32 is provided, constituting a diffusion resisting layer in relation to the gas which is to be measured by means of the polarographic measuring electrode system, i.e. $O_2$. In the area in front of the pH-glass electrode 19, the diffusion resisting layer is omitted as shown in FIG. 1 or, alternatively, as shown in FIG. 2, provided with holes 33 causing substantially no diffusion resistance, so as to constitute a first part of the membrane showing high permeability to $CO_2$ and arranged in front of the exposed measuring surface of the pH-electrode. The two layers 31 and 32 together constitute a second part of the membrane showing low permeability to $O_2$ and arranged in front of the exposed measuring surface of the cathode.

In FIG. 3a, a plane view of a first embodiment of the membrane 30 is shown. The membrane shown in FIG. 3a corresponds to the membrane shown in FIG. 2. As is evident from FIG. 3, the holes 33 are provided as perforations of the area of the inner layer 32 in front of the pH-glass electrode so that the area of the holes 33 constitutes 50-70% of the total area in front of the pH-glass electrode 19. Furthermore, the holes 33 provide a spacer effect in front of the pH-glass electrode.

In FIG. 3b, a plane view of a second, preferred embodiment of the membrane 30 is shown, corresponding to the membrane shown in FIG. 1. The diffusion resisting layer or the inner layer 31 is provided with a central aperture 34 adapted to be arranged in front of the pH-glass electrode 19 as shown in FIG. 1. Within the central aperture 34 or, alternatively, within the holes 33, an enzyme, such as carbonic acid anhydrase, may be arranged.

The membrane 30 may be produced by arranging the two layers 31 and 32 of the membrane 30 on top of one another. Alternatively, the two layers 31 and 32 may be laminated together. In one method for producing the membrane 30, the holes 33 of the embodiment shown in FIG. 3a or, alternatively, the larger central aperture 34 of the embodiment shown in FIG. 3b may be provided prior to arranging the two layers together. In another method for producing the membrane 30, the holes 33 are Laser shot after the layers 31 and 32 have been arranged together. By this second method of producing the membrane 30, the holes 33 are basically crater-shaped so that the edges of the crater-shaped holes provide an additional spacer effect when the membrane is mounted in front of the lower surface of the electrode device 10.

In FIGS. 4 and 5, a membrane mounting tool 40 is shown which is adapted to cooperate with the electrode device 10 for mounting the membrane 30 and the O-ring 27 thereon. In FIG. 4, the membrane mounting tool 40 is shown in an inactivated position prior to mounting the membrane 30 and the O-ring 27 on the electrode device 10. The membrane mounting tool 40 comprises an outer tubular body 41 which is adapted to cooperate with partly a membrane fixing ring 42 and partly an inner tubular body 43. The membrane 30 is fixed between the outer tubular body 41 and the membrane fixing ring 42 which are press fitted into one another. The outer tubular body 41 is provided with longitudinally extending slots 44 which are provided with restrictions 45, 46, and 47 and adapted to cooperate with externally projecting cams 48 of the inner tubular body 43. In the inactivated position of the membrane mounting tool 40 shown in FIG. 4, the cams 48 are arranged within the restrictions 46 and 47 of the slots 44 and, thus, the two tubular bodies 41 and 42 are attached releasably to one another. Cast integrally with the inner tubular body 43, a slotted tube 49 projects into the interior space defined within the two tubular bodies. Within the slotted tube 49, a hollow piston body 50 is arranged having a hollow, substantially frustoconical upper part and a hollow, substantially cylindrical lower part. At the upper end of the piston body 50, i.e. at the upper end of the hollow, substantially frustoconical upper part thereof, a press pad 51 is arranged. In the position of the membrane mounting tool 40 shown in FIG. 4, i.e. when the cams 48 are resting within the restrictions 46 and 47, the press pad 51 rests at the lower surface of the membrane 30. The O-ring 27 is maintained at the lower boundary of the hollow substantially frusto-conical upper part of the piston body 50 in a substantially unstretched condition and rests at the upper end of the slotted tube 49.

Prior to introducing the electrode device 10 into the membrane mounting tool 40, one or two drops of the electrolyte solution 28 is applied on the outer, lower surface of the electrode body 18. When the electrode device 10 is introduced in the membrane mounting tool 40, the lower surface of the electrode body 18 having a few drops of the electrolyte solution 28 applied on its outer, lower surface is brought into contact with the upper surface of the membrane 30. When pressing the electrode device 10 down into the membrane mounting tool 40, the cams 48 are brought out of contact with the restrictions 46 and the outer tubular body 41 is allowed to move downwards guided by the cams 48 and the slots 44.

When pressing the electrode device 10 down into the membrane mounting tool 40 and thus moving the outer tubular body 41 relative to the lower tubular body 43, the piston body 50 is pressed into the interior of the slotted tube 49 while maintaining the membrane 30 in a fixed position relative to the lower surface of the electrode body 18. The press pad 51 provides conformity between the lower surface of the electrode body and the membrane 30. When the piston body 50 is pressed into the interior of the slotted tube 49, the slotted tube 49 is forced to expand and forces the O-ring 27 to expand in conformity to the outer surface of the upper substantially frustro-conical part of the piston body 50.

In FIG. 5 the membrane mounting tool 40 is shown in a position in which the O-ring 27 is brought into contact with the lower surface of the membrane 30 and in which the cams 48 are brought into contact with the restrictions 45 of the slots 44. Therefore, slightly increased force has to be applied to the electrode device 10 in order to force the cams 48 past the restrictions 45 and into a so-called snap-fitting. By this, the fixing of the membrane 30 between the outer tubular body 41 and the membrane fixing ring 42 breaks, and the O-ring 27 is snapfitted into the annular recess 26 while the membrane 30 is applied in a fixed condition relative to the lower surface of the electrode body 18 controlled by the press pad 51.

It should be noticed that the membrane 30 together with the membrane fixing ring 42 and a top part of the outer tubular body 41, cooperating with the membrane fixing ring 42, may be provided as a separate component adapted to cooperate with the remaining components of the membrane mounting tool 40 when mounting the membrane 30 on the electrode device.

EXAMPLE

In a preferred embodiment of the invention shown in FIG. 1 and FIG. 2, the electrode body was a silver body having a chlorinated lower surface and an outer diametre of 9 mm. The pH-glass electrode was arranged in a 4.5 mm hole of the silver body and comprised a main tube made of lead glass and a glass-membrane melted onto the main tube. Within the pH-glass electrode an interior electrolyte solution and a reference electrode were arranged. The interior electrolyte solution had a composition of: 0.5M phenylphosphonic acid, 0.75M NaOH, and 0.01M NaCl. pH=6.84 (25° C.). The interior reference electrode of the pH-glass electrode was a silver conductor of a thickness of 0.25 mm immersed in the interior electrolyte solution of the pH-glass electrode. The cathode assembly comprised a 25 $\mu$m platinum wire embedded within a glass tube made of lead glass having an outer diametre of 1.4 mm. The compensation electrode comprised a 100 $\mu$m platinum wire embedded within a glass tube made of lead glass also having an outer diametre of 1.4 mm. The O-ring was a neoprene O-ring, and the electrode housing was an acrylonitril-butadiene-styrene (ABS) electrode housing of Radiometer type. The membrane consisted of a basic membrane layer made of polyrtetrafluoroethylene (PTFE) of a thickness of 12 $\mu$m. The oxygen diffusion restricting inner layer was made of polypropylene of a thickness of 15 $\mu$m and had an aperture corresponding to the exposed outer surface area of the pH-glass electrode, i.e. an aperture of a diametre of 4.5 mm. The electrolyte solution had a composition of 41% propyleneglycol (1,2-propanediol), 42.5% glycerine (1,2,3-propanetriol), 16.5% water, and $KHCO_3/KCl$ 20/100 m mol/liter all the above percentages are by weight. Two drops of the electrolyte solution were applied on the outer surface of the electrode body prior to arranging the membrane in the above described manner. When arranging a membrane on the lower surface of the electrode device, excessive liquid was pressed out and approximately 10 $\mu l$ electrolyte solution remained within the space defined between the lower surface of the electrode device and the membrane.

The Zener diode had a zener voltage $V_{ze}=12$ V, and the NTC resistor was a 5.6 k$\Omega$ NTC resistor. The polarization voltage of the $O_2$ electrode system was 680 mV, and the sensitivity of the $O_2$ electrode system was 5 pA/mm Hg determined by calibrating the electrode device by means of a gas mixture of known composition, i.e. 5% $CO_2$ in atmospheric air.

In FIG. 6, two diagrammes are shown indicating the time response characteristics of the $CO_2$ and $O_2$-measuring systems of an elecrochemical measuring electrode device including a membrane of known construction and of an electrochemical measuring electrode device according the invention, respectively. The diagrammes were obtained by means of a recording apparatus of type Radiometer TCR 2 while the $O_2$-measuring electrode system was connected to an apparatus of type Radiometer TCM 1 also serving thermostating purposes and while the $CO_2$-measuring electrode system was connected to an apparatus of type Radiometer TCM 10. The known membrane comprised a basic membrane layer of silicon rubber of a thickness of 25 $\mu$m and an $O_2$-diffusion restricting inner layer of polyvinylchloride (PVC) of a thickness of 50 $\mu$m. This known membrane assembly is basically of the kind described in the above-mentioned article: "Investigation of transcutaneous $O_2$—$CO_2$ sensors and their application on human adults and newborns", by Anthony V. Beran et al. Published in: "Birth defects: Original Article Series", Volume XV, number 4, pages 421–430. Copyright 1979 The National Foundation. The membrane of the electrochemical measuring electrode device according to the invention was of the kind described above, i.e. a membrane comprising a basic membrane layer made of polytetrafluoroethylene (PTFE) of a thickness of 12 μm and a $O_2$ diffusion restricting layer made of polypropylene of a thickness of 15 μm. The two curves, one in solid line and one in dotted line designating the $CO_2$-response curve and the $O_2$-response curve, respectively, shown in the upper part of FIG. 6 were obtained using the above described conventionally constructed membrane assembly, and the two curves, one in solid line and one in dotted line, shown in the lower part of FIG. 6 were obtained using the membrane according to the invention, the electrode device being subjected to a known gas composition change. Firstly, the electrode device was exposed to a gas of a content of 5% $CO_2$, 10% $O_2$ and 85% $N_2$. Secondly, the electrode device was exposed to a gas of a content of 8, 21% $CO_2$ and 92, 79% $O_2$.

As is evident from FIG. 6, the time constants of the $CO_2$-measuring system and of the $O_2$-measuring system, designated $t_1$ and $t_2$, respectively, of the electrochemical measuring electrode device including a known membrane are significantly different. The time constant $t_1$ is of the order of 0.5 min., and the time constant $t_2$ is of the order of 10 min. Contrary to this, the time constants of the $CO_2$-measuring system and of the $O_2$-measuring system of the electrochemical electrode device according to the invention, designated $t_3$ and $t_4$, respectively, are basically identical. Thus, the time constants $t_3$ and $t_4$ are of the order of 0.5 min.

Figure 7:
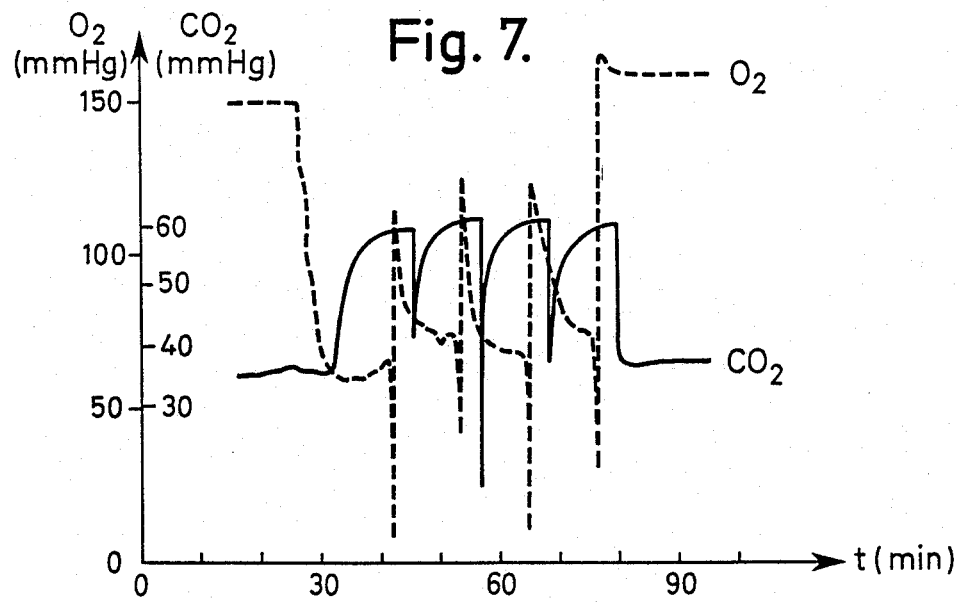

In FIG. 7, two curves are shown, one in dotted line and one in solid line indicating the $O_2$- and $CO_2$-responses, respectively, obtained by means of the electrochemical measuring electrode device according to the invention when connected to the apparatus mentioned above in connection with FIG. 6 and when measuring in vivo. The curves shown in FIG. 7 were obtained in the following manner: One single electrochemical measuring electrode device of a serie of four was employed while thermostated to a temperature of 44° C. On the forearm of a test person, four fixing rings of the above mentioned type were arranged close to one another, whereafter two or three drops of a contact liquid of a composition of 50% propyleneglycol and 50% water were applied within the fixing rings. Thereafter, the electrode device was mounted in a first fixing ring and allowed to substantially reach steady state. Whereupon, the electrode device was moved to a second fixing ring and allowed to substantially reach steady state and so forth. Consequently, the curves shown in FIG. 7 exhibit 4 individual sections. However, as evident from FIG. 7, the first section of the $O_2$-response and $CO_2$-response curves represents a longer period of time compared to the second, third and fourth section of the response curves since hyperthermi had to be generated in the skin area of the test person's forearm prior to reaching steady state. The offset of the two curves shown in FIG. 7 is caused by a pen offset of the recording apparatus used for recording the curves.

It should be noticed that both measuring systems of the electrochemical measuring electrode device according to the invention are free of hysteresis, and that the two curves are basically uniform as should be expected from the above-mentioned time constants determined in vitro and shown in FIG. 6. The downwardly directed spikes of the $O_2$-curve as caused by disturbances when dismounting the electrochemical measuring electrode device from its fixing ring and moving it to another fixing ring.

I claim:

1. An electrochemical measuring electrode device for simultaneously measuring the partial pressures of two gases in a medium of limited gas availability, a first gas partial pressure being measured potentiometrically and a second gas partial pressure being measured polarographically, comprising:
   (a) an electrode body;
   (b) a membrane arranged in front of said electrode body, the electrode body and the membrane together defining a space therebetween;
   (c) an electrolyte solution enclosed in said space;
   (d) a first electrode system for potentiometric measurement arranged in said body, said first electrode system having a reference electrode and a pH-electrode;
   (e) a second electrode system for polarographic measurement arranged in said body, said second electrode system having a cathode and an anode;
   said electrolyte solution communicating with said two electrode systems,
   said membrane comprising
   (i) a first part being permeable to the first gas, arranged in front of the exposed measuring surface of the pH-electrode of said first electrode system and, together with said first electrode system and said electrolyte solution, constituting a first measuring system for measuring the partial pressure of the first gas; and
   (ii) a second part being permeable to the second gas, arranged in front of the exposed measuring surface of the cathode of said second electrode system and, together with said second electrode system and said electrolyte solution, constituting a second measuring system for measuring the partial pressure of said second gas;
   the permeability of said second part of said membrane to the second gas being less than the permeability of said first part of said membrane to the second gas, and the permeabilities of said first and second parts of said membrane being such that said first and second measuring systems have response time characteristics differing from each other at the most by a factor of 10.

2. An electrochemical measuring electrode device according to claim 1, wherein the dimensions of the exposed measuring surface of the cathode and the permeability of the second part of the membrane to the second gas are so adapted to one another that the response of the second measuring system when measuring in a medium of limited gas availability differs from the response of the second measuring system when measuring in a medium of unlimited gas availability at the most by a factor of 0.85.

3. An electrochemical measuring electrode device according to claim 1, wherein said cathode is a microcathode.

4. An electrochemical measuring electrode device according to claim 3, wherein the second membrane part comprises a polypropylene layer of a thickness of 5–30 μm.

5. An electrochemical measuring device according to claim 1, wherein the membrane consists of a base membrane layer and a covering which covers part of the base membrane layer, an uncovered area of the base membrane layer constituting the first membrane part, and a covered area of the base membrane layer together with its covering constituting the second membrane part.

6. An electrochemical measuring electrode device according to claim 5 wherein said covering is an annular covering.

7. An electrochemical measuring electrode device according to claim 5 wherein said covering is arranged between the base membrane layer and the electrode body.

8. An electrochemical measuring electrode device according to claim 7, wherein the uncovered area of the base membrane layer is spaced from the electrode body by means of a spacer constituted by a perforated area of the covering.

9. An electrochemical measuring electrode device according to claim 8, wherein said perforation area of the spacer constitutes at least 50%.

10. An electrochemical measuring electrode device according to claim 1, wherein the first membrane part is made of polytetrafluoroethylene (PTFE) or fluoroethylenepropylene (FEP) of a thickness of less than 50 $\mu$m.

11. The electrochemical measuring electrode device according to claim 10 wherein said thickness is 8 to 50 $\mu$m.

12. An electrochemical measuring electrode device according to claim 1, wherein the second membrane part comprises a polypropylene layer of a thickness of 5-30 $\mu$m.

13. An electrochemical measuring electrode device according to claim 1, wherein the reference electrode of the first electrode system and the anode of the second electrode system are constituted by the electrode body.

14. An electrochemical measuring electrode device according to claim 13, wherein the electrode body is a silver body having a chlorinated surface facing the electrolyte solution, and the cathode is a platinum wire cathode of a diameter of less than 75 $\mu$m.

15. An electrochemical measuring electrode device according to claim 1, wherein said device is adapted for transcutaneous measurement of the partial pressures of $CO_2$ and $O_2$, said electrochemical measuring electrode device including thermosetting means for thermostatically controlled heating of the device to a predetermined temperature.

16. A membrane for an electrochemical measuring electrode device for simultaneously measuring the partial pressures of two gases in a medium of limited gas availability, a first gas being measured potentiometrically, and a second gas being measured polarographically, comprising:

a first part showing permeability to the first gas and adapted to be arranged in front of an exposed measuring surface of a pH-electrode of a potentiometric pH-measuring electrode system and, together with the potentiometric pH-measuring electrode system and an electrolyte solution, to constitute a first measuring system for measuring the partial pressure of the first gas, and a second part showing permeability to the second gas and adapted to be arranged in front of an exposed measuring surface of a cathode of a polarographic electrode system and, together with the polarographic electrode system and the electrolyte solution, to constitute a second measuring system for measuring the partial pressure of the second gas, said permeability of the second part of the membrane to the second gas is less than the permeability of the first part of the membrane to the second gas, and in that the first and the second parts, respectively, of the membrane are adapted to provide response time characteristics of the first and second measuring systems differing from each other at the most by a factor of 10.

17. A membrane according to claim 16, wherein the permeability of the second part is so adapted relative to the dimensions of the exposed measuring surface of the cathode that the response of the second measuring system when measuring in a medium of limited gas availability differs from the response of the second measuring system when measuring in a medium of unlimited gas availability at the most by a factor of 0.85.

18. A membrane according to claims 16 or 17, wherein said membrane consists of a base membrane layer and a covering which covers part of the base membrane layer, an uncovered area of the base membrane layer constituting the first membrane part, and a covered area of the base membrane layer together with its covering constituting the second membrane part.

19. A membrane according to claim 18, wherein the covering is an annular covering.

20. A membrane according to claim 19, wherein the first membrane part comprises polytetrafluoroethylene (PTFE) or fluoroethylene propylene (FEP) of a thickness of less than 50 $\mu$m.

21. A membrane according to claim 19, wherein the second membrane part comprises a polypropylene layer of a thickness of 5-30 $\mu$m.

22. A membrane according to claim 16 wherein the first membrane part is made of polytetrafluoroethylene (PTFE) or fluoroethylenepropylene (FEP) of a thickness of less than 50 $\mu$m.

23. A membrane according to claim 16, wherein the second membrane part is made of a polypropylene layer of a thickness of 5-30 $\mu$m.

* * * * *

UNITED STATES PATENT AND TRADEMARK OFFICE
CERTIFICATE OF CORRECTION

PATENT NO. : 4,836,907

DATED : June 6, 1989

INVENTOR(S) : KNUD G. PEDERSON

It is certified that error appears in the above-identified patent and that said Letters Patent is hereby corrected as shown below:

Column 1, line 4: Change "GASSES" to --GASES--.

Column 1, line 14: Change "gasses" to --gases--.

Column 2, line 1: Change "gasses" to --gases--.

Column 2, line 25: After "cathode" insert a comma (,).

Column 2, line 66: Change "gasses" to --gases--.

Column 3, line 14: "an electrolyte solution ... and a membrane," should be the start of a new sentence.

Column 3, line 66: After "factor" insert --of--.

Column 4, line 2: After "factor" insert --of--.

Column 4, line 19-20: Change "polarographical" to --polarographic--.

Column 4, line 22: Change "it" to --its--.

Column 4, line 54-55: Change "trancsutaneous" to --transcutaneous--.

Column 4, line 65: Change "permability" to --permeability--.

Column 5, line 9: Change "silicon" to --silicone--.

UNITED STATES PATENT AND TRADEMARK OFFICE
CERTIFICATE OF CORRECTION

PATENT NO. : 4,836,907

DATED : June 6, 1989

INVENTOR(S) : KNUD G. PEDERSON

It is certified that error appears in the above-identified patent and that said Letters Patent is hereby corrected as shown below:

Column 5, line 18: Before "thickness" insert --(--.

Column 5, line 54: Change "cmm Hg" to --cm Hg--.

Column 5, line 57: Change "laye" to --layer--.

Column 5, line 66: After "uncovered" insert --area of the basic membrane layer may be spaced from the electrode--.

Column 6, line 21: Change "transutaneous" to --transcutaneous--.

Column 6, line 26: Change "thermosetting" to --thermostating--.

Column 6, line 31: Change "Adult" to --Adults--.

Column 7, line 40: Change "gasses" to --gases--.

Column 7, line 59: Change "gasses" to --gases--.

Column 8, line 29: Delete --corresponding to Fig. 4--.

Column 8, line 49: Change "plastics" to --plastic--.

Column 8, line 66: Delete --up--.

UNITED STATES PATENT AND TRADEMARK OFFICE
CERTIFICATE OF CORRECTION

PATENT NO. : 4,836,907

DATED : June 6, 1989

INVENTOR(S) : KNUD G. PEDERSON

It is certified that error appears in the above-identified patent and that said Letters Patent is hereby corrected as shown below:

Column 9, line 16:   Change "by" to --of--.

Column 9, line 32:   Change "an" to --a--.

Column 9, line 47:   Change "socalled" to --so-called--.

Column 10, line 14:   Change "plane" to --plan--.

Column 10, line 22:   Change "plane" to --plan--.

Column 11, line 57:   Change "noticed" to --noted--.

Column 12, line 21:   Change "polyrtetrafluoroethylene" to --polytetrafluoroethylene--.

Column 12, line 48:   Change "elecrochemical" to --electrochemical--.

Column 12, line 51:   After "according" insert --to--.

Column 12, line 59:   Change "silicon" to --silicone--.

Column 13, line 5:   Before "$O_2$", change "a" to --an--.

Column 13, line 40:   Change "serie" to --series--.

UNITED STATES PATENT AND TRADEMARK OFFICE
CERTIFICATE OF CORRECTION

PATENT NO. : 4,836,907
DATED : June 6, 1989
INVENTOR(S) : KNUD G. PEDERSON

It is certified that error appears in the above-identified patent and that said Letters Patent is hereby corrected as shown below:

Column 13, line 61: Change "noticed" to --noted--.

Column 13, line 67: Change "as" to --are--.

Column 15, line 44:
change "thermosetting" to --thermostating--.

Abstract, line 8: Before "anode", change "a" to --an--.

Title: Change "GASSES" to --GASES--.

Signed and Sealed this

Sixteenth Day of June, 1992

Attest:

DOUGLAS B. COMER

Attesting Officer     Acting Commissioner of Patents and Trademarks